United States Patent
Joshi et al.

(10) Patent No.: US 11,224,593 B2
(45) Date of Patent: Jan. 18, 2022

(54) HYPERBARIC INJECTION SOLUTION OF ROPIVACAINE HYDROCHLORIDE AND PROCESS FOR PREPARATION THEREOF

(71) Applicant: NEON LABORATORIES LIMITED, Mumbai (IN)

(72) Inventors: Neeta Joshi, Mumbai (IN); Rahul Narkhede, Mumbai (IN)

(73) Assignee: Neon Laboratories Limited, Mumbai (IN)

( * ) Notice: Subject to any disclaimer, the term of this patent is extended or adjusted under 35 U.S.C. 154(b) by 0 days.

(21) Appl. No.: 16/085,347

(22) PCT Filed: Apr. 1, 2016

(86) PCT No.: PCT/IN2016/050100
§ 371 (c)(1),
(2) Date: Sep. 14, 2018

(87) PCT Pub. No.: WO2017/009861
PCT Pub. Date: Jan. 19, 2017

(65) Prior Publication Data
US 2019/0054075 A1 Feb. 21, 2019

(51) Int. Cl.
*A61K 31/445* (2006.01)
*A61K 9/00* (2006.01)
*A61K 47/26* (2006.01)
*A61K 9/08* (2006.01)

(52) U.S. Cl.
CPC .......... *A61K 31/445* (2013.01); *A61K 9/0019* (2013.01); *A61K 9/08* (2013.01); *A61K 47/26* (2013.01)

(58) Field of Classification Search
CPC .... A61K 31/445; A61K 47/26; A61K 9/0019; A61K 9/08
See application file for complete search history.

(56) References Cited

U.S. PATENT DOCUMENTS

| 2009/0036539 A1* | 2/2009 | Mitidieri | A61P 23/00 514/626 |
| 2015/0111923 A1* | 4/2015 | Amselem | A61K 47/10 514/330 |

FOREIGN PATENT DOCUMENTS

| CN | 1626081 A | 6/2005 |
| CN | 1660094 A | 8/2005 |
| CN | 102038651 A | 5/2011 |
| CN | 102552126 A | 7/2012 |
| CN | 102670489 A | 9/2012 |

OTHER PUBLICATIONS

Geng et al. 2011, Chinese Medical Journal, 124 (4), pp. 509-513. (Year: 2011).*
Naropin® (Ropivacaine Hydrochloride) Product Information AstraZeneca (Apr. 13, 2011) (Year: 2011).*
International Search Report and Written Opinion for PCT/IN2016/050100 dated Sep. 7, 2016.
Luck, et al., "Spinal Anaesthesia for elective surgery: a comparison of hyperbaric solutions of racemic bupivacaine, evobupivacaine, and ropivacaine", British Journal of Anaesthesia 101 (5): 701-10 (2008).

* cited by examiner

*Primary Examiner* — Kara R McMillian
(74) *Attorney, Agent, or Firm* — Kramer Amado PC

(57) ABSTRACT

Disclosed herein is hyperbaric solution for injection of Ropivacaine Hydrochloride which comprises Ropivacaine Hydrochloride; a base/acid to adjust the pH and a baricity adjuster to modify Baricity of the injection solution.

19 Claims, No Drawings

HYPERBARIC INJECTION SOLUTION OF ROPIVACAINE HYDROCHLORIDE AND PROCESS FOR PREPARATION THEREOF

TECHNICAL FIELD OF THE INVENTION

The present invention relates to a hyperbaric injection solution of pharmaceutically acceptable salt of Ropivacaine. More particularly, the present invention relates to a stable hyperbaric injection solution of Ropivacaine Hydrochloride comprising; an active ingredient, a baricity adjuster, a base/acid to adjust the pH and water as a vehicle. The invention further relates to the process of preparation of a stable hyperbaric injection of Ropivacaine Hydrochloride.

BACKGROUND AND PRIOR ART

Ropivacaine Hydrochloride is a new long acting amino-amide local anaesthetic agent with Pharmacodynamics, pharmacokinetic properties, which has chemical structure resembling to Bupivacaine Hydrochloride. The name Ropivacaine refers to racemate.

Currently available (Marketed) formulation of Ropivacaine Hydrochloride injection is a sterile solution of Ropivacaine Hydrochloride in water for injections which is isobaric solution. Their duration of anaesthesia in the lumbosacral areas is prolonged significantly. The Hyperbaric solution of Bupivacaine is also available in market.

Hyperbaric solutions have a greater specific gravity than the cerebrospinal fluid often making the spread of anaesthesia more predictable with greater spread in the direction of gravity. Hyperbaric solutions gravitate to the thoracic kyphosis in the supine patient, therefore assuring an adequate level of spinal anesthesia, which is T-6 in the average patient.

Hyperbaric Ropivacaine solution gravitates to dependent areas and provides reliable spinal anaesthesia of shorter duration than bupivacaine. The recovery profile of Ropivacaine may be useful where prompt mobilization is required.

Since Bupivacaine has long duration of sensory blockade with delayed return of motor activity and prolongs postanesthesia care unit stay after delivery.

For surgical procedure performed on patients who are not in the supine position, the baricity of the local anaesthetic solution and gravity are employed to direct the local anaesthetic towards the spinal nerves innervating the surgical site.

Hyperbaric Roupivacaine solution will provide a more rapid onset and greater spread of anasthesia but a shorter duration of anaesthesia and analgesia. Thus this solution is primarily useful for abdominal surgery procedures of limited duration.

In the above context, there are few arts which state the anaesthetic effect of Ropivacaine.

J. F. Kuck, P. D. W. Fettes and J. A. Wildsmith in 'Spinal Anaesthesia for Elective surgery: A comparison of hyperbaric solution of racemic Bupivacaine, Levobupivacaine and Ropivacaine' states that, Hyperbaric Ropivacaine provides reliable spinal anaesthesia of shorter duration than Bupivacaine or Levobupivacaine, both of which are clinically indistinguishable. The recovery profile of Ropivacaine may be useful where prompt mobilization is required.

Dr. Feroz Ahmad Dar and Dr. Neelofar Jan in 'Evaluation of Hyperbaric spinal Ropivacaine in lower limb and hip surgery: A comparison with hyperbaric Bupivacaine' states that, a solution of Ropivacaine (hyperbaric) can be used for anaesthesia and is comparable with hyperbaric Bupivacaine in terms of block, but has shorter recovery profile.

CN1660094A discloses the invention related to a freeze-dried powder injection of Ropivacine hydrochloride which is prepared from Ropivacaine hydrochloride and pharmacologically supporting materials including material, lactose, glucose, and dextran. It's preparing process features use of low-tempt aseptic vacuum spray drying for shortening time.

CN1626081 discloses a freeze-dried injection of Ropivacaine which is prepared from the Ropivacaine methanesulfonate (or hydrochloride), diluent chosen from mannitol, lactose, sodium chloride, dextran, glucose, glycine, hydrolytic gelatin and povidone, isotonic regulator and pH regulator through dissolving them in the water for injection, stirring, cooling, adding the water for injection, adding activated carbon, adsorption, filtering for removing carbon, filtering by millipore filter and freeze drying.

CN102670489B discloses Ropivacaine hydrochloride and sodium chloride injection and preparation methods thereof. The process steps including carbon adsorption, coarse filter, fine filter, filling, sterilization, light inspection and packaging process steps. The prepared hydrochloric acid Ropivacaine clear efficacy of sodium chloride injection, measurement results safe; stability test of the indicators are in line with the provisions of, and to address the Ropivacaine water injections require multiple injections, inconvenient to use; freeze-dried powder tends to increase secondary pollution and other defects, particularly suitable for use in patients with analgesia pump; large capacity utilization, so that liquid to maintain a stable concentration timely; not only produce significant postoperative analgesia demand but decline opioids significantly; and the patient can quickly enhance the effect by pressing their own administration.

CN102552126B discloses a high-security Ropivacaine hydrochloride and its preparation method. The high Ropivacaine hydrochloride injection safety formula consisting of: Ropivacaine hydrochloride 20-200 g, sodium chloride 70-100 g, or the amount of hydrochloric acid, sodium hydroxide, and water for injection was added to 10000 ml; the formula is made into 1000 injections, and pH of the injection is 4.0-6.0. This product has good stability, high drug content, and the effect is safe and reliable.

CN102038651B discloses a mesylate Ropivacaine freeze-dried powder, the freeze-dried powder consist of Ropivacaine mesylate and PH regulator and prepared by freeze-drying method uses: (1) sub-IQF stage: the filling good Mesylate Ropivacaine solution was maintained at 10~30 min 0° C., 1~2 h and then kept at −35° C.~−45° C.; (2) sublimation drying stage: the degree of vacuum 10~20 Pa, temperature 2~10° C./h warmed to 0° C. rear holder 1~3 h; (3) Analytical drying stage: the degree of vacuum in the 0~10 Pa, temperature 5~10° C./h was raised to 30° C., and maintained for 2~5 h. The obtained Freez-dried powder has a high yield, good soluble complex, more stable quality and so on.

In view of the above, there is still a need to develop the hyperbaric solution for injection of Ropivacaine for making the spread of anaesthesia more predictable with greater spread in the direction of gravity and stable during its shelf life.

Therefore, it is the object of the present invention to provide a stable hyperbaric solution for Injection of Ropivacaine.

SUMMARY OF THE INVENTION

In accordance with the objective, the present invention provides a stable hyperbaric solution for injection of pharmaceutically acceptable salt of Ropivacaine Hydrochloride.

In a preferred aspect, the present invention provides a stable hyperbaric solution for injection comprising Ropivacaine Hydrochloride; a baricity adjuster to make solution hyperbaric, a base/acid to adjust the pH and water as a vehicle.

In another preferred aspect, the invention provides a process for preparation of said stable hyperbaric injection solution of Ropivacaine Hydrochloride.

DETAILED DESCRIPTION OF THE INVENTION

The invention will now be described in detail in connection with certain preferred and optional embodiments, so that various aspects thereof may be more fully understood and appreciated.

The main rational of the present invention is to provide more rapid onset and greater spread of anasthesia but a shorter duration of anaesthesia and analgesia. Thus this solution is primarily useful for abdominal surgery procedures of limited duration.

According to present invention Ropivacaine may be provided in hyperbaric solution for injection for spinal anaesthesia.

Hyperbaric solutions have a greater specific gravity than the cerebrospinal fluid often making the spread of anaesthesia more predictable with greater spread in the direction of gravity. Hyperbaric solutions gravitate to the thoracic kyphosis in the supine patient, therefore assuring an adequate level of spinal anesthesia, which is T-6 in the average patient.

Hyperbaric Ropivacaine solution gravitates to dependent areas and provides reliable spinal anaesthesia of shorter duration than bupivacaine. The recovery profile of Ropivacaine may be useful where prompt mobilization is required. Since Bupivacaine has long duration of sensory blockade with delayed return of motor activity and prolongs postanesthesia care unit stay after delivery.

For surgical procedure performed on patients who are not in the supine position, the baricity of the local anaesthetic solution and gravity are employed to direct the local anaesthetic towards the spinal nerves innervating the surgical site.

The present invention provides a stable hyperbaric solution for injection of Ropivacaine Hydrochloride comprising pharmaceutically acceptable salt of Ropivacaine Hydrochloride, a baricity adjuster to make solution hyperbaric, a base/acid to adjust the pH and water as a vehicle.

Accordingly, in a preferred embodiment, the instant invention provides a stable hyperbaric solution for injection of Ropivacaine Hydrochloride comprising Ropivacaine Hydrochloride; a baricity adjuster such as Sucrose in the form of Mannitol or Dextrose; a base/acid to adjust the pH and water as a vehicle.

The Ropivacaine Hydrochloride used in hyperbaric solution is present in an amount of 5 mg.

The Dextrose used in hyperbaric solution is present in an amount of 2% w/v to 25% w/v, preferably, 4% w/v to 15% w/v.

Mannitol used in hyperbaric solution is present in an amount of 5% w/v to 10% w/v.

The pH of hyperbaric solution is adjusted with base/acid such as potassium hydroxide or sodium hydroxide/Glacial acetic acid or hydrochloric acid, preferably, sodium hydroxide or Hydrochloric acid.

The pH of hyperbaric solution is maintained between 3.5 to 6.0, preferably between 4.0 to 6.0.

The present invention provides a process for preparation of a stable hyperbaric solution for injection of Ropivacaine Hydrochloride comprises, dissolving baricity adjuster in water, followed by addition of API; adjusting the pH of the solution between 4 to 6 using a base/acid and making the required volume with cool water to obtain the injection.

Accordingly, in another preferred embodiment, the present invention provides a process for preparation of a stable hyperbaric solution for injection of Ropivacaine Hydrochloride comprises;
 a) Dissolving Dextrose or Mannitol in water followed by addition of Ropivacaine Hydrochloride;
 b) adjusting the pH of the solution of step (a) between 4.0 to 6.0 using a sodium hydroxide or Hydrochloric acid and
 c) making the required volume with cool water to obtain the injection.

In another embodiment, a hyperbaric solution of Ropivacaine Hydrochloride according to invention comprises 4% w/v to 15% w/v Dextrose to make the solution hyperbaric.

In yet another embodiment, a hyperbaric solution of Ropivacaine Hydrochloride according to the invention, wherein, the 4% w/v to 15% w/v Dextrose is dissolved in aqueous vehicle.

In another embodiment, a hyperbaric solution of Ropivacaine Hydrochloride according to invention comprises 5% w/v to 10% w/v mannitol to make the solution hyperbaric.

Several different trials were conducted & tested for stability. Some of these trials are discussed below in brief.

EXAMPLES

The following examples, which include preferred embodiments, will serve to illustrate the practice of this invention, it being understood that the particulars shown are by way of examples and for purpose of illustrative discussion of preferred embodiments of the invention.

Example 1

| Ingredient | Quantity/mL |
|---|---|
| Ropivacaine Hydrochloride | 5 mg |
| Mannitol | 5% w/v |
| Sodium Hydroxide/Hydrochloric acid | q.s. to pH 4.0 to 6.0 |
| Water For Injections | q.s. to 1 ml |

Procedure:
a) Dissolving Mannitol in a cool water, followed by addition of Ropivacaine Hydrochloride and adjusting pH of the solution to 4.0 to 6.0 with solution of Sodium Hydroxide or Hydrochloric acid;
b) making up the required volume with cool water for injections.

The results are discussed in Table 1 herein below:

TABLE 1

| Stage | Assay % | Baricity | Chromatography Impurity Limit of 2,6-Dimethylaniline (Ropivacaine related compound A) N.M.T. 0.1% |
|---|---|---|---|
| Initial | 102.65 | Hyperbaric | Nil |
| 1M/25° C. | 103.56 | Hyperbaric | Nil |
| 2M/25° C. | 103.49 | Hyperbaric | Nil |

TABLE 1-continued

| Stage | Assay % | Baricity | Chromatography Impurity Limit of 2,6-Dimethylaniline (Ropivacaine related compound A) N.M.T. 0.1% |
|---|---|---|---|
| 3M/25° C. | 101.13 | Hyperbaric | Nil |
| 1M/40° C. | 103.93 | Hyperbaric | Nil |
| 2M/40° C. | 102.80 | Hyperbaric | Nil |
| 3M/40° C. | 101.57 | Hyperbaric | Nil |

Example 2

| Ingredient | Quantity/mL |
|---|---|
| Ropivacaine Hydrochloride | 5 mg |
| Mannitol | 10% w/v |
| Sodium Hydroxide/Hydrochloric acid | q.s. to pH 4.0 to 6.0 |
| Water For Injections | q.s. to 1 ml |

Procedure:

a) Dissolving Mannitol in a cool water, followed by addition of Ropivacaine Hydrochloride and adjusting pH of the solution to 4.0 to 6.0 using solution of Sodium Hydroxide or Hydrochloric acid;

b) making up the required volume with cool water for injections.

The results are discussed in Table 2 herein below:

TABLE 2

| Stage | Assay % | Baricity | Chromatography Impurity Limit of 2,6-Dimethylaniline (Ropivacaine related compound A) N.M.T. 0.1% |
|---|---|---|---|
| Initial | 104.28 | Hyperbaric | Nil |
| 1M/25° C. | 103.71 | Hyperbaric | Nil |
| 2M/25° C. | 102.34 | Hyperbaric | Nil |
| 3M/25° C. | 105.06 | Hyperbaric | Nil |
| 1M/40° C. | 103.76 | Hyperbaric | Nil |
| 2M/40° C. | 105.21 | Hyperbaric | Nil |
| 3M/40° C. | 103.41 | Hyperbaric | Nil |

Example 3

| Ingredient | Quantity/mL |
|---|---|
| Ropivacaine Hydrochloride | 5 mg |
| Dextrose | 5% w/v |
| Sodium Hydroxide/Hydrochloric acid | q.s. to pH 4.0 to 6.0 |
| Water For Injections | q.s. to 1 ml |

Procedure:

a) Dissolving Dextrose in a cool water, followed by addition of Ropivacaine Hydrochloride and adjusting pH of the solution to 4.0 to 6.0 using solution of Sodium Hydroxide or Hydrochloric acid;

b) making up the required volume with cool water for injections.

The results are discussed in Table 3 herein below:

TABLE 3

| Stage | Assay % | Baricity | Chromatography Impurity Limit of 2,6-Dimethylaniline (Ropivacaine related compound A) N.M.T. 0.1% |
|---|---|---|---|
| Initial | 102.40 | Hyperbaric | Nil |
| 1M/25° C. | 101.08 | Hyperbaric | Nil |
| 2M/25° C. | 102.19 | Hyperbaric | Nil |
| 3M/25° C. | 104.63 | Hyperbaric | Nil |
| 1M/40° C. | 104.17 | Hyperbaric | Nil |
| 2M/40° C. | 103.94 | Hyperbaric | Nil |
| 3M/40° C. | 104.50 | Hyperbaric | Nil |

Example 4

| Ingredient | Quantity/mL |
|---|---|
| Ropivacaine Hydrochloride | 5 mg |
| Dextrose | 8% w/v |
| Sodium Hydroxide/Hydrochloric acid | q.s. to pH 4.0 to 6.0 |
| Water For Injections | q.s. to 1 ml |

Procedure:

a) Dissolving Dextrose in a cool water, followed by addition of Ropivacaine Hydrochloride and adjusting pH of the solution to 4.0 to 6.0 using solution of Sodium Hydroxide or Hydrochloric acid;

b) making up the required volume with cool water for injections.

The results are discussed in Table 4 herein below:

TABLE 4

| Stage | Assay % | Baricity | Chromatography Impurity Limit of 2,6-Dimethylaniline (Ropivacaine related compound A) N.M.T. 0.1% |
|---|---|---|---|
| Initial |  | Hyperbaric | Nil |
| 1M/25° C. | 103.67 | Hyperbaric | Nil |
| 2M/25° C. | 101.63 | Hyperbaric | Nil |
| 3M/25° C. | 100.35 | Hyperbaric | Nil |
| 1M/40° C. | 103.55 | Hyperbaric | Nil |
| 2M/40° C. | 100.29 | Hyperbaric | Nil |
| 3M/40° C. | 99.97 | Hyperbaric | Nil |

Example 5

| Ingredient | Quantity/mL |
|---|---|
| Ropivacaine Hydrochloride | 5 mg |
| Dextrose | 10% w/v |
| Sodium Hydroxide/Hydrochloric acid | q.s. to pH 4.0 to 6.0 |
| Water For Injections | q.s. to 1 ml |

Procedure:

a) Dissolving Dextrose in a cool water, followed by addition of Ropivacaine Hydrochloride and adjusting pH of the solution to 4.0 to 6.0 using solution of Sodium Hydroxide or Hydrochloric acid;

b) making up the required volume with cool water for injections.

The results are discussed in Table 5 herein below:

TABLE 5

| Stage | Assay % | Baricity | Chromatography Impurity Limit of 2,6-Dimethylaniline (Ropivacaine related compound A) N.M.T. 0.1% |
|---|---|---|---|
| Initial | 105.13 | Hyperbaric | Nil |
| 1M/25° C. | 104.34 | Hyperbaric | Nil |
| 2M/25° C. | 103.63 | Hyperbaric | Nil |
| 3M/25° C. | 104.92 | Hyperbaric | Nil |
| 1M/40° C. | 104.64 | Hyperbaric | Nil |
| 2M/40° C. | 103.57 | Hyperbaric | Nil |
| 3M/40° C. | 102.83 | Hyperbaric | Nil |

We claim:

1. A stable hyperbaric injection solution of Ropivacaine, comprising;
   a) a pharmaceutically acceptable salt of Ropivacaine;
   b) a baricity adjuster to make the hyperbaric injection solution hyperbaric;
   c) a pH adjuster comprising a base, an acid, or a mixture thereof; and
   d) an aqueous vehicle;
      wherein no 2,6-dimethylaniline is observed in the hyperbaric injection solution of Ropivacaine after storage for one to three months at a temperature of 25° C. to 40° C.;
      wherein the stable hyperbaric injection solution of Ropivacaine is made by a process comprising adding the pharmaceutically acceptable salt of Ropivacaine to a solution of the baricity adjuster;
      wherein the stable hyperbaric injection solution of Ropivacaine has a pH of 3.5 to 6.

2. The stable hyperbaric injection solution of claim 1, wherein the baricity adjuster is Mannitol, Dextrose, or a mixture thereof.

3. The stable hyperbaric injection solution of claim 2; wherein the baricity adjuster is Dextrose.

4. The stable hyperbaric injection solution of claim 3, wherein the Dextrose is present in an amount of 2% w/v to 25% w/v.

5. The stable hyperbaric injection solution of claim 4, wherein the Dextrose is present in an amount of 4% w/v to 15% w/v.

6. The stable hyperbaric injection solution of claim 2, wherein the baricity adjuster is Mannitol.

7. The stable hyperbaric injection solution of claim 6, wherein the Mannitol is present in an amount of 5% w/v to 10/ow/v.

8. The stable hyperbaric injection solution of claim 1, wherein the pH adjuster is selected from the group consisting of potassium hydroxide, sodium hydroxide, Glacial acetic acid, hydrochloric acid, and a mixture thereof.

9. The stable hyperbaric injection solution of claim 1, wherein the pH of the solution is between 4.0 and 6.0.

10. The stable hyperbaric injection solution of claim 1, wherein the pharmaceutically acceptable salt of Ropivacaine is a hydrochloride salt of Ropivacaine.

11. A process for preparation of a stable hyperbaric injection solution of claim 1, comprising:
    a) forming a solution by dissolving the baricity adjuster in water, followed by addition of the pharmaceutically acceptable salt of Ropivacaine;
    b) adjusting the pH of the solution to between 3.5 and 6.0; and
    c) adding a required volume of water to the solution to obtain the hyperbaric injection solution.

12. The process of claim 11, wherein the process involves addition of a hydrochloride salt of Ropivacaine.

13. The process of claim 11, wherein the baricity adjuster is Dextrose; and the Dextrose is used in an amount of 2% w/v to 25% w/v.

14. The process of claim 13, wherein the Dextrose is used in an amount of 4% w/v to 15% w/v.

15. The process of claim 11, wherein the baricity adjuster is Mannitol; and the Mannitol is used in an amount of 5% w/v to 10/ow/v.

16. The process of claim 11, wherein the pH is adjusted with sodium hydroxide and/or hydrochloric acid.

17. The process of claim 11, wherein the pH of the solution is adjusted to between 3.5 and 6.0.

18. A stable hyperbaric injection solution of Ropivacaine, comprising;
    a) a pharmaceutically acceptable salt of Ropivacaine at an initial concentration;
    b) 2% w/v to 25% w/v of Dextrose to make the hyperbaric injection solution hyperbaric;
    c) a pH adjuster comprising a base, an acid, or a mixture thereof; and
    d) an aqueous vehicle;
       wherein an actual concentration of Ropivacaine in the hyperbaric injection solution remains at the initial concentration after storage for one to three months at a temperature of 25° C. to 40° C.;
       wherein the stable hyperbaric injection solution of Ropivacaine has a pH of 3.5 to 6, and is made by a process comprising adding the pharmaceutically acceptable salt of Ropivacaine to a solution of the dextrose.

19. A stable hyperbaric injection solution of Ropivacaine, comprising;
    a) a pharmaceutically acceptable salt of Ropivacaine;
    b) 2% w/v to 25% w/v of Dextrose to make the solution hyperbaric;
    c) a pH adjuster selected from the group consisting of
       potassium hydroxide or sodium hydroxide,
       glacial acetic acid or hydrochloric acid, and
       mixtures thereof; and
    d) an aqueous vehicle;
       wherein no 2,6-dimethylaniline is observed in the hyperbaric injection solution of Ropivacaine after storage for one to three months at a temperature of 40° C.;
       wherein the stable hyperbaric injection solution of Ropivacaine is made by a process comprising adding the pharmaceutically acceptable salt of Ropivacaine to a solution of the dextrose.

* * * * *